United States Patent [19]

Varadaraj et al.

[11] Patent Number: 5,716,839
[45] Date of Patent: Feb. 10, 1998

[54] PHYTOADDITIVES FOR ENHANCED SOIL BIOREMEDIATION

[75] Inventors: Ramesh Varadaraj, Flemington; David William Savage, Lebanon, both of N.J.

[73] Assignee: Exxon Research and Engineering Company, Florham Park, N.J.

[21] Appl. No.: 542,590

[22] Filed: Oct. 13, 1995

[51] Int. Cl.$^6$ .................................................. C12S 1/00
[52] U.S. Cl. .................... 435/262; 435/262.5; 435/277; 435/281
[58] Field of Search .............................. 435/262, 262.5, 435/281, 277

[56] References Cited

U.S. PATENT DOCUMENTS

| | | | |
|---|---|---|---|
| 4,721,585 | 1/1988 | Santolini et al. | 435/262 |
| 4,891,320 | 1/1990 | Aust et al. | 435/262 |
| 5,476,788 | 12/1995 | Lamar | 435/262 |

FOREIGN PATENT DOCUMENTS 9119039  12/1991  WIPO ........................ 435/262

*Primary Examiner*—Helen Pratt
*Attorney, Agent, or Firm*—Joseph J. Dvorak; Jay Simon

[57] ABSTRACT

A bioremediation process is provided comprising adding cedar pieces to a hydrocarbon contaminated soil in an amount ranging from about 5 to about 15 wt. % based on the weight of the contaminated soil and applying sufficient nitrogen and phosphorous nutrients to the soil to provide a C:N:P ratio in the range of about 100:10:1 to about 100:1:0.1.

8 Claims, 1 Drawing Sheet

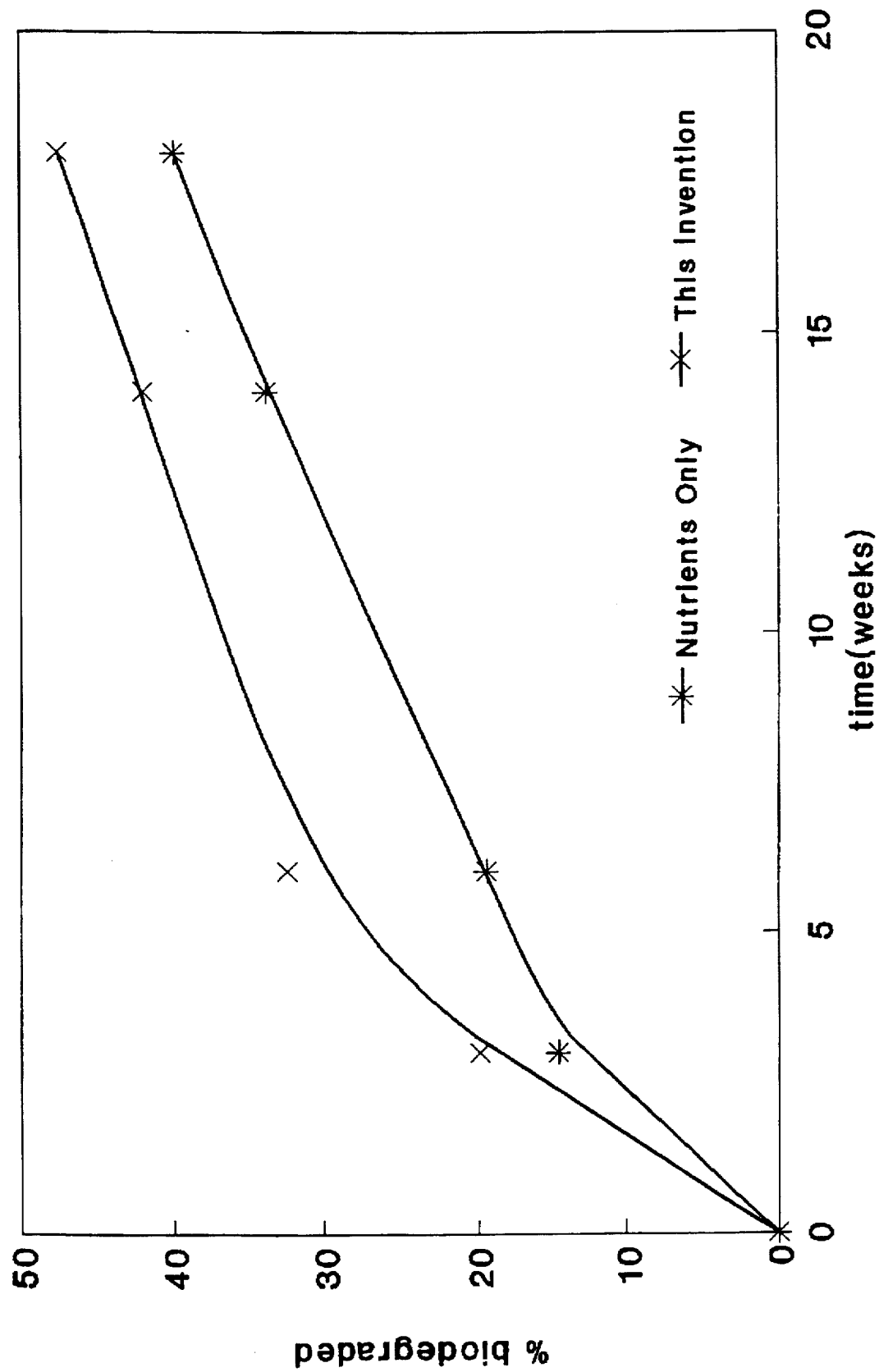

PHYTOADDITIVES FOR ENHANCED SOIL BIOREMEDIATION

FIELD OF THE INVENTION

The present invention relates to microbial remediation of hydrocarbon contaminated soil.

BACKGROUND OF THE INVENTION

As is well known, there are several microbial species found in soil that are capable of assimilating petroleum hydrocarbons. Unfortunately, the rate of microbial assimilation of petroleum hydrocarbons is relatively slow. It is necessary, therefore, to stimulate the microbial assimilation if bioremediation is to be utilized in removing such pollutants from soil. Thus, microbial nutrients, especially nitrogen containing nutrients like urea have been added to contaminated soil as a method for enhancing the biodegradation of petroleum contaminants. Although this approach has been useful, increasing the rate of biodegradation even further remains highly desirable.

Accordingly, it is an object of the present invention to improve the rate of biodegradation of hydrocarbon contaminated soil.

SUMMARY OF THE INVENTION

Simply stated, a bioremediation process is provided comprising adding cedar pieces to a hydrocarbon contaminated soil in an amount ranging from about 5 to about 15 wt. % based on the weight of the contaminated soil and applying sufficient nitrogen and phosphorous nutrients to the soil to provide a C:N:P ratio in the range of about 100:10:1 to about 100:1:0.1.

This and other embodiments of the present invention will become more apparent upon a reading of the detailed description which follows.

BRIEF DESCRIPTION OF THE DRAWING

The accompanying FIGURE compares the percent of biodegradation vs. time for a hydrocarbon contaminated soil treated in accordance with this invention with one which has been nutriated with nitrogen and phosphorous nutrients only.

DETAILED DESCRIPTION OF THE INVENTION

Although any hydrocarbon contaminated soil may be treated in accordance with this invention, the invention is particularly applicable for weathered hydrocarbon contaminants on soil.

Thus, a hydrocarbon contaminated soil is bioremediated in accordance with the present invention by applying to the soil pieces of cedar in amounts ranging from about 5 to about 15 wt. % based on the weight of the contaminated soil and applying to the soil nitrogen and phosphorous nutrients in an amount sufficient to provide a C:N:P ratio in the range of from about 100:10:1 to about 100:1:0.1.

As is well known, the term cedar includes a wide range of coniferous evergreens that have a characteristic odor and a red or red-tinged durable wood. Included within the term cedar, for the purposes of this invention is the botanically similar evergreen, cypress. Specific examples of coniferous evergreens useful in the practice of the present invention are Arborvitae, *Juniperus virgininia*, *Chamaecyparis thyoides*, *C.lawsoniania*, *C.nootbatensis*, *Cedries libani*, *C.atlantica*, and the like.

By pieces is meant fragments, chips, threads and the like. Indeed, especially suitable are the shredded barks and leaves of cedars.

It is particularly preferred in the practice of the present invention that the cedar be mixed with the soil to which it has been applied. This can be done in an appropriate mixer or it can be done by spreading the cedar over a plot of contaminated soil, followed by tilling, for example, tilling to a depth of about 2 feet.

In the practice of the present invention, it is particularly preferred that the soil being treated also contain nitrogen and phosphorous in amounts sufficient to provide a C:N:P ratio generally in the range of about to 100:10:1 to about 100:1:0.1 preferably in the range of about 100:2:0.2 to about 100:2:1. The nitrogen and phosphorous nutrients may be applied as pellets, in aqueous solution or as coated controlled release nutrients.

Particularly preferred in the practice of the present invention is to apply the nitrogen and phosphorous nutrients to the contaminated soil in an aqueous media by spraying or the like. In general, the nitrogen and phosphorous nutrients in an aqueous media will be applied to the soil after first applying and mixing the pieces of cedar with the soil; however, the nitrogen and phosphorous nutrients may also be applied simultaneously with the cedar or just prior to the application of the cedar to the soil. Typical microbial nutrients include urea, potassium nitrate, calcium nitrate, ammonium nitrate, ammonium phosphate, sodium phosphate and the like.

Optionally and preferably after applying the cedar and nutrients to the contaminated soil, the moisture content of the soil is maintained at a level of about 15 to 20 wt. % of its holding capacity typically for a time sufficient for at least a portion of the hydrocarbon to be biodegraded and preferably for as long as biodegradation continues.

The following examples demonstrate that the addition of pieces of cedar to hydrocarbon contaminated soil in accordance with the present invention, enhances the rate of biodegradation of the hydrocarbons in the soil.

EXAMPLE 1

A plastic pan 12 inches long by 8 inches wide was filled with 2 kilograms of hydrocarbon contaminated soil. To the contaminated soil was added shredded cedar bark at a treat rate of 10 wt. % of shredded cedar bark to the weight of the soil. The cedar bark was mixed into the soil by hand tilling.

Next an aqueous solution of urea and ammonium dihydrogen phosphate was added such that a C:N:P ratio of 100:2.0:0.2 was obtained followed by hand-tilling. The pans were watered and hand-tilled weekly. The amount of water applied was sufficient to provide a moisture content of about 17 wt. %.

The percent petroleum hydrocarbons biodegraded was determined for each of Example 1 and Comparative Example 1 using EPA method 418.1 with the following modifications:

1. The soil sample size was increased to 30 grams.
2. The acidification step specified in the test was eliminated.
3. The amount of drying agent required by the test was increased to assure effective drying.
4. The drying agent used was magnesium sulfate.
5. A four-hour time period for soxhlet extraction was employed.
6. The amount of silica gel was increased.

The results are graphically presented in the accompanying FIGURE.

Comparative Example 1

In this Example the general procedure outlined in Example 1 was followed except that pieces of cedar were not added to the soil.

EXAMPLE 2

10 g of soil from each of the soil pans in Example 1 and Comparative Example 1 after 3 weeks of treatment was removed and placed in respirometry cells.

The two respirometry cells were attached to an automated Micro-Oxymax respirometer sold by Columbus Instruments International Corporation, Columbus, Ohio, and the oxygen uptake determined every 2 hours for 3 weeks for each of the samples. Oxygen uptake values for the cedar treated soil sample was corrected for respiration due to cedar bark and the results of the experiment is shown in Table 1. The uptake of oxygen (or respiration) is a measure of biodegradation occurring in the samples.

TABLE 1

| Soil Treatment | Oxygen uptake in 2.5 weeks (mg. of oxygen) |
| --- | --- |
| Example 1 | 3.604 |
| Comparative Example 1 | 2.467 |

What is claimed is:

1. A soil bioremediation consisting essentially of applying cedar pieces to a hydrocarbon contaminated soil in an amount ranging from about 5 wt. % to 15 wt. % based on the weight of the hydrocarbon contaminated soil and applying nitrogen and phosphorous nutrients in an amount sufficient to provide a C:N:P ratio in the range of about 100:10:1 to about 100:1:0.1.

2. The process of claim 1 including maintaining the moisture level of the soil at about 15 to about 20 wt. % of its holding capacity.

3. The process of claim 2 including mixing the cedar pieces in the soil.

4. The process of claim 3 wherein the cedar is selected from the group consisting of Arborvitae, *Juniperus virgininia, Chamaecyparis thyoides, C.lawsoniania, C.nootbatensis, Cedries libani, C.atlantica* and the mixture thereof.

5. The process of claim 4 wherein the nutrients are applied to the soil in an aqueous solution.

6. In the process of bioremediating a hydrocarbon contaminated soil by applying microbial nutrients to the soil, the improvement consisting essentially of:

applying cedar pieces to the soil in an amount ranging from about 5 wt. % to about 15 wt. % based on the weight of the hydrocarbon contaminated soil and mixing the pieces in the soil.

7. The improvement of claim 6 wherein the cedar is selected from the group consisting of Arborvitae, *Juniperus virgininia, Chamaecyparis thyoides, C.lawsoniania, C.nootbatensis, Cedries libani, C.atlantica* and the mixture thereof.

8. The improvement of claim 7 including maintaining the moisture level of the soil at about 15 to about 20 wt. % of its holding capacity.

* * * * *